US006649805B1

(12) United States Patent
Carlucci et al.

(10) Patent No.: US 6,649,805 B1
(45) Date of Patent: Nov. 18, 2003

(54) ARTICLES WITH ODOR CONTROL

(75) Inventors: Giovanni Carlucci, Chieti (IT); Achille Di Cintio, Pescara (IT); Alessandro Gagliardini, Jesi (IT); Stefano Scialla, Rome (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/914,497

(22) PCT Filed: Mar. 2, 2000

(86) PCT No.: PCT/US00/05503

§ 371 (c)(1),
(2), (4) Date: Aug. 29, 2001

(87) PCT Pub. No.: WO00/51657

PCT Pub. Date: Sep. 8, 2000

(30) Foreign Application Priority Data

Mar. 5, 1999 (EP) ............................................. 99103928

(51) Int. Cl.[7] ................................................. A61F 13/15
(52) U.S. Cl. ....................................... 604/359; 604/360
(58) Field of Search .................................. 604/359, 360

(56) References Cited

U.S. PATENT DOCUMENTS 5,061,807 A     10/1991    Gethoffer et al.
5,306,487 A   *  4/1994    Karapasha et al.

FOREIGN PATENT DOCUMENTS

| EP | 0 399 584 A2 | 11/1990 |
| EP | 0 510 619 A1 | 10/1992 |
| EP | 0 895 777 A2 | 2/1999 |
| WO | WO 92/11238 A2 | 7/1992 |
| WO | WO 97/00354 A1 | 1/1997 |

* cited by examiner

Primary Examiner—Dennis Ruhl
(74) Attorney, Agent, or Firm—Bridget D. Ammons; Kevin C. Johnson

(57) ABSTRACT

The present invention relates to a disposable absorbent articles like sanitary napkins and pantiliners having a peroxyacid for controlling odors associated with body fluids. The disposable absorbent article includes a liquid pervious topsheet, a backsheet, an absorbent core intermediate to the backsheet and said topsheet and a peroxyacid. One of the peroxyacids utilized in the disposable absorbent article is epsilon-pthalimido peroxyhexanoic acid.

7 Claims, No Drawings

ARTICLES WITH ODOR CONTROL

FIELD OF THE INVENTION

This invention relates to articles, such as absorbent articles, for controlling odour, especially the odour associated with bodily fluids, comprising, as the odour control material, the particular peroxyacids as defined herein, and to the use of these peroxyacids as defined herein after as an odour control material.

BACKGROUND OF THE INVENTION

Malodours may be present in the environment from numerous sources both animate and inanimate. Many products and articles are available which aim to avoid or minimise the detection of such odours. In particular, it is particularly desirable to provide odour control materials to address the malodours which are generated by the human body, or from bodily fluids such as perspiration, urine, faeces, menstrual fluids, vaginal fluids and the like.

Articles like absorbent articles for example are designed to be worn by humans to absorb bodily fluids, such as urine, menstrual fluid and perspiration, etc. Examples of absorbent articles include sanitary napkins, pantiliners, disposable diapers, incontinence pads, tampons, perspiration pads, and the like.

In use, the absorbent articles are known to acquire a variety of compounds, for example volatile fatty acids (e.g. isovaleric acid), ammonia, amines (e.g. triethylamine), sulphur containing compounds (e.g. mercaptans, sulphides), alcohols, ketones and aldehydes (e.g., furaldehyde) which release unpleasant odours. These compounds may be present in the bodily fluid or may be developed by chemical reactions and/or any fluid degradation mechanisms once the bodily fluid is absorbed into the absorbent article like for example a feminine pad. In addition bodily fluids usually contain microorganisms and/or enzymes that can also generate malodorous by products as a result of degradation mechanisms like putrefactive degradation, acid degradation, proteins degradation, fat degradation and the like. Unpleasant odours which emanate from absorbent pads when in use may make the wearer feel self conscious.

Various odour control materials have been disclosed in the art to combat some of the unpleasant odours referred to above. Indeed solutions have been provided that use different technical approaches like masking, i.e., covering the odor with a perfume, or absorbing the odour already present in the bodily fluids and those generated after degradation, or preventing the formation of the odour.

Most of the focus in the prior art is found on the odour absorption technology. Examples of these types of compounds include activated carbons, clays, zeolites, silicates, absorbing gelling materials, starches, cyclodextrine, ion exchange resins and various mixture thereof as for example described in EP-A-348 978, EP-A-510 619, WO 91/12029, WO 91/11977, WO89/02698, and/or WO 91/12030. All of these types of odour control agents are believed to control odour by mechanisms whereby the malodorous compounds and their precursors are physically absorbed by the agents and thereby hinder the exit of the odour from articles like absorbent articles. However, such mechanisms are not completely effective as the formation of the odour itself is not prevented and thus odour detection is not completely avoided.

Thus although these materials provide some control of odours associated with bodily fluids, there still exists a need of further improvement in terms of odour control on a wide range of malodorous compounds.

It is an object of the present invention to provide effective odour control over a wider range of malodorous compounds. More particularly, it is an object of the present invention to provide articles, especially disposable absorbent articles, which deliver a broader spectrum of odour control mainly by preventing the formation of malodours.

It has now been found that the above needs can be addressed by using a peroxyacid, preferably $\epsilon$-phtalimido peroxyhexanoic acid (PAP) as the odour control material for an article, preferably a disposable absorbent article.

By the present invention it has been surprisingly discovered that the use of the peroxyacids of the present invention in an article, like an absorbent article coming into contact with bodily fluids, results in significant decrease of bodily odour, as compared to the same article without the odour control material according to the present invention. Indeed, it is speculated that the peroxyacids according to the present invention have a dual odour control mechanism: they are able to prevent the generation of odour by blocking enzymatic and/or microbial activity as well as to combat the odours already present by oxidising them into no-smelling molecules.

Indeed in contrast to the use of some inorganic peroxides like persulfate or percarbonate, the peroxyacids as described herein are free of deactivation by catalase and/or peroxidase enzymes that are present in bodily fluids. Thus, the peroxyacids according to the present invention are able to keep/retain their oxidizing capacity to oxidise oxidable malodorous compounds into no-smelling compounds.

An additional advantage of the peroxyacids described herein is that the generation of malodorous smelling by products like chlorine derivatives and ammonium derivatives is avoided, when they come into contact with bodily fluids. Indeed, in contrast to the peroxyacids described herein other oxidants like persulphate, periodate, percarbonate, and/or perborate oxidize the chlorides usually present in bodily fluids like menstruation into chlorine derivatives that are not acceptable from the consumer from an odour point of view. Also in contrast to the peroxyacids described herein other oxidants like urea peroxides, calcium peroxides, strontium peroxides and/or barium peroxides (i.e., compounds having an alkaline pH) promote the formation of malodours ammonia derivatives, one of the by products of proteins degradation occurring in, the bodily fluids when they come into contact therewith.

A further advantage associated with the peroxyacid according to the present invention is that it also provides the absorbent article into which it has been incorporated with a better feeling and more acceptable cleanness level. Indeed, the present invention provides an absorbent article capable of changing the color of the menstruation (red blood color) to a pale red color and even to a whitish color.

It is yet another advantage of the present invention that the peroxyacid used herein as the odour control material, ensures prolonged shelf life time of the absorbent article where it is contained in comparison to other oxidants like alkali metal peroxides (e.g., sodium, potassium, lithium, cerium peroxides) and/or superoxide salts (e.g., sodium , potassium, rubidium, cerium, calcium, strontium, barium superoxides). Indeed, it has been surprisingly found that the peroxyacid as described herein present in the absorbent article of the present invention does not react readily with carbon dioxide or vapour air, and thus retains its whole ability to control malodour for a prolonged period of time, up to the time when the absorbent article is used, i.e., comes into contact with bodily fluids.

Whereas the present invention is preferably directed to absorbent articles like pantiliners, feminine napkins, incontinent pads, diapers, tampons, interlabial pads, perspiration pads, surgical pads, breast pads and the like, other articles may include the peroxyacids as described herein too for the purpose of effective odour control. Indeed, other applications include other articles designed to be worn in contact with the body such as clothing, bandages, thermal pads, acne pads, cold pads, compresses, surgical pads/dressings and the like, body and household cleansing articles like impregnated wipes (e.g. baby wipes, wipes for feminine intimate hygiene), impregnated tissues, towels, articles for absorbing perspiration such as shoe insoles, shirt inserts, carpets and the like, and articles for animals like litters and the like.

BACKGROUND ART OF THE INVENTION

U.S. Pat. No. 4,363,322 discloses deodorising and disinfecting liquid-absorbing products such as a sanitary napkin, a compress or a diaper, comprising a liquid absorbing material and inside the product at a distance from its outer edges a substance which gives off oxygen in contact with moisture like peroxides, ozonides, superoxides, oxo-ozonides and the like. This reference does not disclose the peroxyacids according the present invention, let alone the odour controlling benefit associated thereto.

SUMMARY OF THE INVENTION

The present invention relates to an article, preferably a disposable absorbent article, for controlling odour, preferably the odour associated with bodily fluids, comprising a peroxyacid according to the formula:

R-CO3H wherein R is a substituted or unsubstituted, saturated or unsaturated, linear or branched hydrocarbon group having from 1 to 25 carbon atoms or a cyclic group having from 3 to 32 carbon atoms and optionally at least one hetero atom (Preferably an heterocyclic group) or a cyclic alkyl group having from 4 to 32 carbon atoms and optionally at least one hetero atom (preferably an heterocyclic alkyl group) or a mixture thereof.

The present invention also encompasses the use as an odour control material of a peroxyacid according to the above formula.

DETAILED DESCRIPTION OF THE INVENTION

The articles according to the present invention, for controlling odours, especially odours associated with bodily fluids, comprise as an essential element a peroxyacid according to the formula described herein after.

As used herein "odor" and "odour" have the exact same meaning as known to those skilled in the art.

By "article" it is meant herein any tridimentional solid material being able to receive/carry a peroxyacid as described herein after. Preferred articles according to the present invention are disposable absorbent articles that are designed to be worn in contact to the body of a user and to receive fluids discharged from the body, such as disposable absorbent pantiliners, sanitary napkins, catamenials, incontinence inserts/pads, diapers, tampons, interlabial pads/ inserts, breast pads and the like. Other articles suitable according to the present invention also include other articles designed to be worn in contact with the body such as clothing, bandages, thermal pads, acne pads, cold pads, compresses, surgical pads/dressings and the like, articles for absorbing perspiration such as shoe insoles, shirt inserts, perspiration pads and the like, body and household cleansing articles like impregnated wipes (e.g. baby wipes, wipes for feminine intimate hygiene), impregnated tissues, towels, and the like, and articles for animals like litters and the like.

By "bodily fluids" it is meant herein any fluids produced by human or animal body occurring naturally or accidentally like for instance in the case of skin cutting, including for instance perspiration, urine, menstrual fluids, faeces, vaginal secretions and the like.

The peroxyacids to be used herein are according to the following formula:

R-CO3H wherein R is a substituted or unsubstituted, saturated or unsaturated, linear or branched hydrocarbon group having from 1 to 25 carbon atoms or a cyclic group having from 3 to 32 carbon atoms and optionally at least one heteroatom or a cyclic alkyl group having from 4 to 32 carbon atoms and optionally at least one heteroatom.

Typically R is a substituted or unsubstituted, linear or branched alkyl group or alkenyl group having from 1 to 25 carbon atoms, more preferably from 1 to 14 carbon atoms, even more preferably from 3 to 10, and most preferably from 4 to 6. R may also typically be an aryl group having from 3 to 32 carbon atoms, preferably from 3 to 25, more preferably from 6 to 20, even more preferably from 8 to 15 carbons atoms, or an aryl alkyl group having from 4 to 32 total carbon atoms, preferably from 4 to 25, more preferably from 6 to 20 and even more preferably from 8 to 13, or an heterocyclic group containing from 3 to 32 carbon atoms, preferably from 3 to 25, more preferably from 3 to 20 carbon atoms, even more preferably from 5 to 15 and from 1 to 5 hetero atoms, preferably 1 to 3, wherein the hetero atoms are independently selected from the group consisting of oxygen, nitrogen and sulfur, and preferably is nitrogen or oxygen, or an heterocyclic alkyl group containing from 4 to 32 total carbon atoms, preferably from 4 to 25, more preferably from 4 to 22, even more preferably from 6 to 18 and from 1 to 5 hetero atoms, preferably 1 to 3, wherein the hetero atoms are independently selected from the group consisting of oxygen, nitrogen and sulfur, and preferably is nitrogen or oxygen.

The preferred peroxyacids according to the present invention are those wherein R is a cyclic group or cyclic alkyl group, preferably a heterocyclic group or heterocyclic alkyl group.

Even more preferred herein are the peroxyacids according to the following formulae:

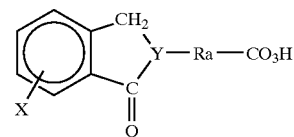

or

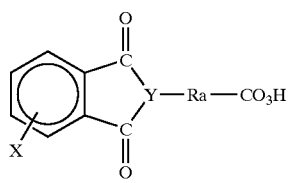

wherein Ra is a substituted or unsubstituted, saturated or unsaturated, linear or branched hydrocarbon group having from 1 to 14 carbon atoms, Y is an heteroatom and X are substituents in position ortho or meta independently selected from the group of hydrogen, hydroxy, halogen, carboxy, aliphatic saturated or unsaturated, linear or branched, hydrocarbon group having from 1 to 10 carbon atoms.

Preferably Ra is a substituted or unsubstituted, linear or branched alkyl group or alkenyl group having from 2 to 12 carbon atoms, preferably from 2 to 10, more preferably from 2 to 8, even more preferably from 3 to 6 and most preferably 5 carbon atoms. Preferably Y is an heteroatom selected from the group consisting of oxygen, nitrogen and sulfur, and more preferably is nitrogen atom (>N-). Preferably X are substituents on position ortho or meta independently selected from the group consisting of hydrogen, hydroxy, aliphatic linear or branched alkyl group or alkenyl group having from 1 to 10 carbon atoms, preferably from 2 to 7 and most preferably from 3 to 5 carbon atoms. Highly preferred herein all the substituents X are independently hydrogen.

The preferred peroxyacids for use according to the present invention are phthalimido and phtalamido peroxyalkanoic acids.

Highly preferred herein is E-phthalimido peroxyhexanoic acid which may be commercially available from AUSIMONT under the name PAP, or EURECO 0 (in granule form), Eureco WKC (in wet granule form) or Eureco, HC (in powdered active form).

It has now surprisingly been found that the peroxyacids according to the present invention provide significant odour control capacity, especially versus odour associated with bodily fluids. It is speculated that this benefit is due to a dual mechanism: Firstly they can prevent the generation of the odour by blocking the microbial and/or enzymatic activity. Indeed it is speculated that the peroxyacids as described herein oxidize sensitive sulphidryl and sulphur bonds typically present in enzymes, thereby deactivating the enzymes which otherwise would have contributed to the normal metabolism of the micro-organisms like microbes. It is further speculated that the peroxyacids oxidize double bonds in other metabolites like for instance nutriments (e.g., unsaturated fat) for the micro-organisms, thereby rendering these nutriments inefficient for the microbial growth which otherwise would have resulted in generation of malodorous compounds. It is further believed that the peroxyacids described herein disrupt the chemiosmotic function of the lipoprotein cytoplasmatic membrane of the microbe/bacteria cells and thus disrupt the transport function at the cell walls. This later disruption is especially noticeable with the hydrophobic peroxyacids described herein, like the cyclic or cyclic alkyl peroxyacids namely the ones according to the chemical formulae described herein before. Indeed it is speculated that the heterocyclic group or heterocyclic alkyl group according to the preferred peroxyacids herein are able to better react with the lipoproteins of the cell wall of the micro-organisms.

Secondly the peroxyacids as described herein are able to combat the malodorous compounds already present by oxidising them into non-smelling compounds.

A further important advantage associated with the peroxyacids according to the present invention is that they also provide the absorbent article into which they have been incorporated with a better feeling and more acceptable cleanness level. Indeed, the presence of the peroxyacids according to the present invention provides absorbent articles with controlled odor capacity when the menstruation comes into contact with the article, but also absorbent articles being capable of changing the color of the menstruation (red blood color) to a pale red color and even to a whitish color.

Typically, the articles like disposable absorbent articles comprise the peroxyacid or a mixture thereof at a level of from 1 $gm^{-2}$ to 250 $gm^{-2}$, preferably from 5 to 150 $gm^{-2}$, more preferably from 10 $gm^{-2}$ to 100 $gm^{-2}$ and most preferably from 20 $gm^{-2}$ to 70 $gm^{-2}$.

Optional agents

The articles according to the present invention preferably further comprise on top of the peroxyacid described herein before, other conventional agents or mixtures thereof.

For instance additional odour control agent or combinations thereof, known in the art for this purpose may be used herein. These agents can typically be classified according to the type of odour the agent is intended to combat. Odors may be chemically classified as being acidic, basic or neutral.

Alternatively, the odor control agents may be categorised with respect to the mechanism by which the malodor detection is reduced or prevented. For example, odor control agents which chemically react with malodorous compounds or with compounds which produce malodorous degradation products thereby generating compounds lacking odor or having an odor acceptable to consumers may also be utilized herein.

Suitable odor control agents for use herein typically include carbonates (e.g., sodium carbonate), bicarbonates (e.g., sodium bicarbonate), phosphates (e.g., sodium phosphate), sulphates (e.g., zinc and copper sulphates), carboxylic acids such as citric acid, lauric acid, boric acid, adipic acid and maleic acid, activated carbons, clays, zeolites, silicas, absorbent gelling materials (AGM) and starches. Such odor control agents and systems are disclosed in more details hereinafter and for example in EP-A- 348 978, EP-A- 510 619, WO 91/12029, WO 91/11977, WO 91/12030, WO 81/01643 and WO 96/06589.

Suitable odour control agents also include chelating agents and may be selected from amino carboxylates such as for example ethylenediamine- tetracetate, as described for example in U.S. Pat. No. 4,356,190, amino phosphonates such as ethylenediaminetetrakis (methylene-phosphonates), polyfunctionally-substituted aromatic chelating agents as described in U.S. Pat. No. 3,812,044 and mixtures thereof. Without intending to be bound by theory it is believed that the benefit of these materials is in part due to their exceptional ability to remove iron, copper, calcium, magnesium and manganese ions present in the absorbed fluids and their degradation products by the formation of chelates.

Another suitable odor control agent for use herein is a buffer system, such as citric acid and sodium bicarbonate, sodium phosphate and sorbic acid buffer systems. Also, buffer systems having a pH of from 7 to 10 as described for example in WO94/25077 may be useful herein.

Alternative odor control agents are ion exchange resins such as those described in U.S. Pat. No. 4,289,513 and U.S. Pat. No. 3,340,875.

Masking agents such as perfumes may also be used as odor control agents herein.

Typically, the articles like disposable absorbent articles may comprise the odour control agent or a mixture thereof at a level of from 0.5 gm$^{-2}$ to 600 gm$^{-2}$, preferably from 5 to 500 gm$^{-2}$, more preferably from 10 gm$^{-2}$ to 350 gm$^{-2}$ and most preferably from 20 gm$^{-2}$ to 200 gm$^{-2}$.

Absorbent Gelling Odor Control Materials

As is well-known from recent commercial practice, absorbent gelling materials (sometimes referred to as "supersorbers") are becoming broadly used in absorbent articles. AGM's are materials which have fluid-absorbing properties.

Such materials are highly preferred herein as the optional odor control agent due to their dual function of absorbing fluids and odors.

Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those which, upon contact with fluids (i.e., liquids) such as water or body-fluids, imbibe such fluids and thereby form hydrogels. These preferred absorbent gelling materials will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization". Typically, commercial absorbent gelling materials have a degree of neutralization somewhat less than 90%.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) Which. is needed to reach extraction equilibrium, by then filtering the formed hydrogel from the supematant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue 32,649, The absorbent gelling materials which are especially useful in the absorbent articles herein are those which have an equilibrium extractables content in synthetic urine of no more than about 17%, preferably no more than about 10% by weight of the absorbent gelling material.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 microns are less. desirable. Particles having a smallest dimension larger than about 2mm may also cause a feeling of grittyness in the absorbent article, which is undesirable from a consumer aesthetics standpoint. Furthermore, rate of fluid absorption can be affected by particle size. Larger particles have very much reduced rates of absorption. Preferred for use herein are absorbent gelling material s particles substantially all of which have a particle size of from about 30 microns to about 2 mm. "Particle Size" as used herein means the weighted average of the smallest dimension of the individual particles.

The amount of absorbent gelling material particles used in absorbent article will typically range from 10 gm$^{-2}$ to 150 gm$^{-2}$, preferably from 30 gm$^{-2}$ to 110 gm$^{-2}$, more preferably from 55 gm$^{-2}$ to 85 gm$^{-2}$.

Silica Odor Control Agent

Particularly suitable herein as an additional odor control agent is silica. Silica, i.e. silicon dioxide $SiO_2$ exists in a variety of crystalline forms and amorphous modifications, any of which are suitable for use herein. In particular, silicas having a high surface area or in agglomerated form are preferred. Silica molecular sieves are not considered to be within the definition of silica as used herein. Preferably the silica is in a highly purified form such that. is contains at least 90%, preferably 95%, more preferably 99% silicon dioxide. Most preferably the silica is silica gel having a 100% silica content. Alternatively, the silica may be provided from other sources such as metal silicates including sodium silicate.

Zeolite Odor Control Agent

The use and manufacture of zeolite material is well know in the literature and is described in the following reference texts: ZEOLITE SYNTHESIS, ACS Symposium Series 398, Eds. M. L. Occelli and H. E Robson (1989) pages 2–7; ZEOLITE MOLECULAR SIEVES, Structure, Chemistry and Use, by D. W. Breck, John Wiley and Sons (1974) pages 245–250, 313–314 and 348–352; MODERN APPLICATIONS OF MOLECULAR SIEVE ZEOLITES, Ph.D. Dissertation of S. M. Kuznicki, U. of Utah (1980), available from University of Microfilms International, Ann Arbor, Mich., pages 2–8.

Zeolites are crystalline aluminosilicates of group IA and group IIA elements such as Na, K, Mn, Ca and are chemically represented by the empirical formula:

$$M_{2/n}O \cdot Al_2O_3 \cdot ySiO_2 \cdot wH_2O$$

where y is 2 or greater, n is the cation valence, and w is the water content in the voids of the zeolite.

Structurally, zeolites are complex, crystalline inorganic polymers based on an infinitely extending framework of $AlO_4$ and $SiO_4$ tetrahedra linked to each other by sharing of oxygen ions. This framework structure contains channels or interconnected voids that are occupied by the cations and water molecules.

The structural formula of a zeolite is based on the crystal unit cell, the smallest unit of structure, represented by $$M_{x/n}[(AlO_2)_x(SiO_2)_y] \cdot wH_2O$$

where n is the valence of cation M, w is the number of water molecules per unit cell, x and y are the total number of tedrahedra per unit cell, y/x usually having values of 1–5.

Zeolites may be naturally derived or synthetically manufactured. The synthetic zeolites being preferred for use herein. Suitable zeolites for use herein include zeolite A, zeolite P, zeolite Y, zeolite X, zeolite DAY, zeolite ZSM-5, or mixtures thereof. Most preferred is zeolite A.

According to the present invention the zeolite is preferably hydrophobic. This is typically achieved by increasing the molar ratio of the $SiO_2$ to $AlO_2$ content such that the ratio of x to y is at least 1, preferably from 1 to 500, most preferably from 1 to 6.

The Absorbent Article

The odor control agents (i.e., peroxyacid as described herein and optional additional odor control agent(s)) may be incorporated into the absorbent article by any of the methods disclosed in the art, for example layered on the core of the absorbent article or mixed within the fibres of the absorbent core.

The peroxyacid as described herein and optional additional odor control agent(s) are preferably incorporated between two layers of cellulose tissue. Optionally the system may be bonded between two cellulose tissue layers with, for example, a hot melt adhesive or any suitable bonding system, as described in WO 94/01069.

In one embodiment of the present invention the peroxyacid as described herein and optional additional odor control agent are incorporated in a layered structure in accordance with the disclosure of WO 94/01069 or Italian patent application number TO 93A 001028. TO 93A 001028 describes a layered structure substantially as described in WO 94/01069 with the exception that TO 93A 001028 comprises a much higher quantity of absorbent gelling material in the intermediate layer which is between the fibrous layers (120 gm$^{-2}$) that would be incorporated as an optional component in the present invention. The intermediate layer comprises in particular a polyethylene powder as thermoplastic material which is mixed with the peroxyacid as described herein. The mixture is then heated such that the polyethylene melts and glues the laminate layers together. Adhesive lines are preferably also placed on the edges of the laminate to ensure that the edges of the laminate stick and any loose peroxyacid as described herein and optional additional odor control agent present do not fall out of the laminate.

Alternatively, the polyethylene powder may be replaced by a conventional glue for instance those commercially available from ATO Findley under the name H20–31® to glue the laminate layers and/or components together. Advantageously this method step allows to avoid the heating step necessary when using polyethylene powder.

In a preferred embodiment the peroxyacid as described herein is incorporated between two layers of cellulose tissues separated by another layer of cellulose in order to avoid possible reaction between peroxyacid and the optional additional odor control agent.

The peroxyacid as described herein may be distributed homogeneously or non homogeneously over the entire absorbent article or in at least one layer of the topsheet or in at least one layer of the core or any mixture thereof. The peroxyacid as described herein may be distributed homogeneously or non homogeneously on the whole surface of the desired layer or layers, or on one or several area of the surface layer/layers to which it is positioned (e.g. central area and/or surrounding area like the edges of a layer of the absorbent article) or mixtures thereof. Preferably the peroxyacid is located towards the topsheet or is located in the topsheet itself (preferably the secondary topsheet).

In a preferred embodiment the peroxyacid is positioned such that at least a portion of the fluid discharge comes into contact with said peroxyacid before the additional odor control agent (e.g., AGM) if present. In particular, the peroxyacid is located in a separate layer from the additional odor control agent if present. Preferably the peroxyacid is located towards the topsheet or is located in the topsheet itself (preferably the secondary topsheet) and the odor control agent is located further away from the topsheet than the peroxyacid. In one embodiment of the present invention, the peroxyacid is positioned in at least one of the topsheet layers and the additional odor control agent is positioned in the core if present. More preferably, the peroxyacid is located at the fluid discharge entry point of the absorbent article.

The peroxyacid as described herein and optional odor control agent if present may be incorporated as a powder, a granulate or can be sprayed in the form of for example a peroxyacid-containing solution within the absorbent article. When used in a granulate or particulate form the peroxyacid as described herein and the optional odor control agent may be granulated separately and then mixed together or granulated together.

Absorbent Core

According to the present invention, the absorbent can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

a Primary/Secondary Fluid Distribution Layer

One optional component of the absorbent according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials in combination with suitable carriers.

Suitable carriers include materials which are conventionally utilized in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention may comprise multiple layers comprises a double layer tissue laminate formed by folding the tissue onto itself. These layers can be joined to each other for example by adhesive or by mechanical interlocking or by hydrogen bridge bands. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet. The topsheet may comprise a single layer or a multiplicity of layers. In a preferred embodiment the topsheet comprises a first layer which provides the user facing surface of the topsheet and a second layer between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non woven fabrics and films. In a preferred embodiment of the present invention at least one of the layers, preferably the upper layer, of the topsheet comprises a hydrophobic, liquid permeable apertured polymeric film. Preferably, the upper layer is provided by a film material having apertures which are provided to facilitate liquid transport from the wearer facing surface towards the absorbent structure. If present the lower layer preferably comprises a non woven layer, an apertured formed film or an airlaid tissue.

The Backsheet

The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the Whole of the absorbent structure and can extend into and form part of or all of the preferred sideflaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film typically having a thickness of from about 0.012 mm (0.5 mil) to about 0.051 mm (2.0 mil).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more clothlike appearance. Further, the backsheet can permit vapors to escape from the absorbent structure, i.e. be breathable, while still preventing extrudates from passing through the backsheet. Also breathable backsheets comprising several layers, e.g. film plus non-woven structures, can be used.

The present invention is further illustrated by the following example.

EXAMPLES

Example A

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper which covers the external adhesive layer. The side of the absorbent fibrous core was then exposed by slightly shifting the water impermeable plastic bottom layer and subsequently, the fibrous core was split into two halves, each having approximately the same thickness, along a plane which is parallel to the plane of the napkin itself. The peroxyacid was homogeneously distributed between these tow fibrous layers which were then joined together to reconstitute the absorbent core.

The water impermeable inner backsheet was then put back into its original position and the wrap around perforated coverstock was sealed along the cut by means of e.g. a double sided adhesive tape.

Samples were produced using the method above, containing the odor control system as described hereinbelow.

The peroxyacid (0.8g) used was $\epsilon$-phtalimido peroxyhexanoic acid commercially available from Ausimont.

Example B

Other pads were prepared by following the method in Example A except that absorbing gelling material (AGM) was added on top of the peroxyacid in Example A. Accordingly the peroxyacid and AGM were homogeneously distributed between these two fibrous layers which were then joined together to reconstitute the absorbent core.

The peroxyacid (0.8g) used was $\epsilon$-phtalimido peroxyhexanoic acid commercially available from Ausimont. The AGM (0.8g) used was XZ 9589001, available from Dow Chemicals.

Example C

Other pads were prepared by following the method in Example B except that after having split the fibrous core into two halves, the peroxyacid was homogeneously distributed onto the upper halve fibrous layer (i.e. the fibrous layer halve intended to be closer to the topsheet) and the AGM was homogeneously distributed onto the lower halve fibrous layer (i.e., the one intended to be closer to the backsheet of the pad once reconstituted). Then a layer of airlaid tissue (19 mm*70 mm of low basis weight) available from Fripa under the code/name NCB Tissue HWS was positioned between the two halve fibrous layers which are then joined together to reconstitute the absorbent core. The presence of the airlaid tissue between the two fibrous layer avoids direct contact between the peroxyacid and the AGM.

These samples were produced using as the peroxyacid, 0.8 g of $\epsilon$-phtalimido peroxyhexanoic acid commercially available from Ausimont and AGM (0.8 g) available from Dow Chemicals (XZ 9589001).

All the above exemplified pads delivered outstanding odour control benefits when coming into contact with for example bodily fluids.

What is claimed is:

1. A disposable absorbent article comprising a liquid pervious topsheet, a backsheet, an absorbent core intermediate to the backsheet and said topsheet and a peroxyacid wherein the peroxyacid is according to the formulae:

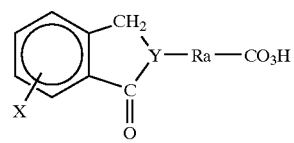

or

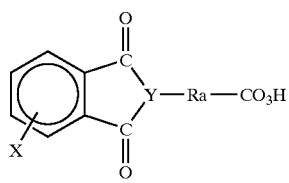

wherein Ra is a substituted or unsubstituted, saturated or unsaturated, linear or branched hydrocarbon group having from 1 to 14 carbon atoms, Y is an heteroatom, preferably selected from the group consisting of oxygen, nitrogen and sulfur and more preferably is nitrogen, and X are substituents in position ortho or meta independently selected from the group of hydrogen, hydroxy, halogen, carboxy, aliphatic saturated or unsaturated, linear or branched, hydrocarbon group having from 1 to 10 carbon atoms, or a mixture thereof.

2. An article according to claim 1 wherein the peroxyacid is a phthalimido peroxyalkanoic acid, a phtalamido peroxyalkanoic acid or a mixture thereof and preferably is ε-phthalimido peroxyhexanoic acid.

3. An article according to claim 1 which comprises from 1 gm–2 to 250 gm–2 of said peroxyacid.

4. An article according to claim 1 which further comprises at least one additional odor control agent.

5. An article according to claim 4, wherein the additional odor control agent is selected from the group consisting of absorbing gelling materials, silicas, zeolites, carbons, starches, chelating agents, pH buffered materials, cyclodextrine and derivatives thereof, chitin, kieseiguhr, clays, ion exchange resins, carbonates, bicarbonates, phosphates, sulphates, carboxylic acids and combination thereof.

6. An article according to claim 5, wherein the additional odor control agent is an absorbent gelling material.

7. An article according to claim 6, which comprises the additional odor control agent or a mixture thereof at a level of 0.5 $gm^{-2}$ to 600 $gm^{-2}$.

* * * * *